(12) United States Patent
Kranner et al.

(10) Patent No.: US 9,393,132 B2
(45) Date of Patent: Jul. 19, 2016

(54) FOOT PROSTHESIS

(71) Applicant: medi GmbH & Co KG, Bayreuth (DE)

(72) Inventors: Werner Kranner, Bad Aibling (DE); Volker Nissels, Bayreuth (DE)

(73) Assignee: MEDI PROSTHETICS GMBH, Bayreuth (DE)

( * ) Notice: Subject to any disclaimer, the term of this patent is extended or adjusted under 35 U.S.C. 154(b) by 98 days.

(21) Appl. No.: 13/851,260

(22) Filed: Mar. 27, 2013

(65) Prior Publication Data

US 2013/0261767 A1  Oct. 3, 2013

(30) Foreign Application Priority Data

Mar. 27, 2012  (DE) .......................... 10 2012 006 023

(51) Int. Cl.
*A61F 2/66* (2006.01)
*A61F 2/50* (2006.01)

(52) U.S. Cl.
CPC ............ *A61F 2/66* (2013.01); *A61F 2002/5009* (2013.01); *A61F 2002/5083* (2013.01); *A61F 2002/6614* (2013.01); *A61F 2002/6657* (2013.01); *A61F 2002/6664* (2013.01); *A61F 2002/6692* (2013.01)

(58) Field of Classification Search
CPC ....... A61F 2/66; A61F 2/6607; A61F 2/6664; A61F 2/6692; A61F 2002/6664; A61F 2002/6692
USPC .......................................... 623/49, 52, 55, 56
See application file for complete search history.

(56) References Cited

U.S. PATENT DOCUMENTS

| | | | |
|---|---|---|---|
| 4,959,073 A * | 9/1990 | Merlette ........................ | 623/55 |
| 5,549,711 A * | 8/1996 | Bryant ........................... | 623/53 |
| 6,572,659 B1 | 6/2003 | Ryan | |
| 6,669,737 B2 * | 12/2003 | Mosler et al. ................... | 623/55 |
| 6,852,132 B1 | 2/2005 | Houser et al. | |
| 6,929,665 B2 * | 8/2005 | Christensen .................... | 623/52 |
| 7,824,446 B2 * | 11/2010 | Christensen .............. | A61F 2/66 623/52 |
| 8,540,781 B2 * | 9/2013 | Nissels et al. ................... | 623/55 |
| 2003/0009238 A1 | 1/2003 | Whayne | |
| 2006/0185703 A1 | 8/2006 | Townsend | |
| 2008/0228288 A1 | 9/2008 | Nelson et al. | |
| 2010/0332002 A1 * | 12/2010 | Nelson ........................... | 623/55 |
| 2011/0029097 A1 | 2/2011 | Ochoa | |

FOREIGN PATENT DOCUMENTS

| | | |
|---|---|---|
| DE | 102010034893 A1 | 2/2012 |
| EP | 2420212 A1 | 2/2012 |
| WO | 0230340 A1 | 4/2002 |

OTHER PUBLICATIONS

English translation of Chinese Office Action, Chinese Patent Application No. 20131010445.4, dated Dec. 17, 2014. 3 pages.

* cited by examiner

*Primary Examiner* — Bruce E Snow
(74) *Attorney, Agent, or Firm* — Lucas & Mercanti, LLP; Klaus P. Stoffel (57) ABSTRACT

Foot prosthesis, comprising an upper part, and a lower part that is placed on the ground when walking, which parts extend one above the other and at a distance from each other, are connected to each other at the forefoot and the heel and, forming a spring, move relative to each other during walking, wherein the upper part (3) and the lower part (4) are formed by means of a one-piece, closed component (2) made from a carbon fiber composite.

16 Claims, 7 Drawing Sheets

FOOT PROSTHESIS

CROSS REFERENCE TO RELATED APPLICATION

This Application claims the priority of DE Patent Application No. 102012006023.8 filed on Mar. 27, 2012, which application is incorporated herein by reference in its entirety.

The invention relates to a foot prosthesis, comprising an upper part, and a lower part that is placed on the ground when walking, which parts extend one above the other and at a distance from each other, are connected to each other at the forefoot and the heel and, forming a spring, move relative to each other during walking.

A foot prosthesis of the kind described allows the wearer to set the foot down in a comfortable manner, damped via the spring properties of the prosthesis, and provides a walking pattern similar to the real foot. Modern foot prostheses are composed, for example, of a carbon laminate, that is to say a carbon fiber composite. They have an upper part, by which the foot prosthesis is coupled via a suitable connecting means, for example a pyramid adapter, to a connecting shaft or the like, with which the entire prosthesis is secured on the leg stump. The upper part extends from the heel area as far as the forefoot. In the area of the forefoot, the upper part is connected to a lower part that is placed on the ground when walking. Upper part and lower part are spaced apart from each other but lie approximately congruently one above the other. In the heel area, upper part and lower part are usually connected via an elastic damping element, for example made of a rubber-like material, which acts as impact damper and damps the force that arises on set-down. That is to say, upper part and lower part end one above the other at the heel and are coupled via the damping element. In the area between this damping element and the forefoot, the upper part and lower part form a spring, which is bent and stressed during walking. In the area of the forefoot, the upper part and lower part can be connected to each other via a separate connection element, for example they can be screwed onto each other, with integration of a damping insert piece. It is also known for the upper part and lower part to be connected directly at the forefoot via a deflection.

The upper part and lower part together form a spring, which compresses when loaded and thus permits comfortable walking. The heel elastomer acts as impact damper and point of rotation between rear foot lever and front foot lever, that is to say between heel area and forefoot area. For a secure connection, the heel elastomer of known prostheses is connected to the upper part and lower part across a relatively large surface area, usually by adhesive bonding. In this way, it is possible to achieve a firm integration of the damping heel elastomer, which is of course subject to considerable loads and has to perform its function over a long period of time. However, the integration of this heel damping element, usually an elastomer block made from an elastomer with a defined Shore A hardness, leads to a shortening of the effective spring lengths in the area of the upper and lower parts and/or of the spring excursions and, consequently, to a reduction in the possibilities of deformation. This effect is intensified if the upper part and lower part are also connected to each other in the area of the forefoot, for example by screwing or adhesive bonding, i.e. then with even shorter spring lengths or spring excursions.

Therefore, the problem addressed by the invention is that of making available an improved foot prosthesis which permits an improved mobility and spring characteristic of upper part and lower part.

To solve this problem in a foot prosthesis of the kind mentioned in the introduction, provision is made, according to the invention, that the upper part and the lower part is formed by means of a one-piece, closed component made from a carbon fiber composite.

In the foot prosthesis according to the invention, the actual prosthesis body, namely the spring composed of upper part and lower part, is formed using only a one-piece, closed component, which is made from a carbon fiber composite, i.e. a carbon laminate. Therefore, this component requires no special connection elements between upper part and lower part, since these are formed in one part on the one-piece, closed carbon component. They are connected to each other by suitable deflections, resulting on the one hand in the spring characteristic and also on other hand in the corresponding mobility relative to each other, which is necessary if reaction forces are to induce deformation during walking. Since no connection elements are needed for coupling upper part and lower part, the maximum spring length or the greatest possible spring excursions can be utilized effectively, i.e. the sole area, that is to say the area of the lower part, can deform homogeneously along the entire length of the foot and can also twist, as a result of which a homogeneous rollover can be guaranteed since, in the course of the step cycle, the flexural strength of the area of the spring, i.e. of the component, momentarily in contact with the ground does not change abruptly. The possibility of being able to utilize the maximum spring lengths or spring excursions has the effect of achieving a sufficient torsional flexibility, which in turn leads to the possibility of balanced pronation and supination of the prosthetic foot and permits good adaptation to different ground surfaces and to unevenness in the ground surface, unlike the case with the upper-part and lower-part configurations that are almost rigidly braced via the connection elements.

The foot prosthesis according to the invention is thus composed only of a spring, namely the one-piece, closed component, and a user with a high degree of mobility is provided with good functionality and energy return.

Indeed, the particular advantage of the foot prosthesis according to the invention with the one-part spring lies in an uninterrupted spring action, i.e. the energy flow is not interrupted by rigid connection points such as screwed connections, adhesively bonded connections and laminations as are obtained in the prior art through the integration at least of the heel damping element, optionally also of the screwed connection at the forefoot end.

As has been be the upper part and the lower part merge into each other in one piece in the spring component. According to the invention, this is achieved by a deflection at the forefoot and at the heel, in each case in the range of between 135° and 180°.

In a particularly expedient refinement of the invention, provision is made that the component, in the area of the upper part near the heel, has a further deflection, in such a way that a first upper-part portion extending above the lower part merges via the deflection into a second upper-part portion extending above the first portion. This second deflection, which is provided on the upper part, forms as it were a further spring portion. A first spring portion is already formed by the deflection from the upper part to the lower part, i.e. via the direct connection of both parts. According to the invention, the upper part is now itself curved in order to form a further deflection, such that two upper-part portions extend one above the other and in so doing form a further spring portion. This upper-part area ultimately has an S shape. During walking, an inward spring movement, i.e. energy storage, also takes place in the area of this further deflection, and also an outward spring movement, i.e. energy return. In the area of the deflection, an elastomer element can be fitted or arranged on one or both of the two upper-part portions.

This elastomer element serves to damp the inward spring movement, i.e., with a sufficient further inward spring movement, one upper-part portion bears on the elastomer element on the other upper-part portion, and the further inward spring movement is additionally damped via the elastomer element.

For further targeted damping of the inward spring movement, a refinement of the invention proposes that, in the area between the upper part and the lower part, an elastomer element is provided that engages around the deflection, provided on the heel-side upper part area by means of the two upper-part portions, and couples the upper part to the lower part, at least during walking, wherein this elastomer element can preferably be inserted releasably. As has been described, the component according to the invention forming the foot prosthesis is a closed component. If, as has been described, the upper-part area near the heel is formed via the deflection as a spring portion, i.e. with a virtual S shape, it is then possible, in this embodiment of the invention, for a further elastomer element, to be integrated in the "component interior" and engage around the deflection. During walking, the upper part travels inward relative to the lower part when the prosthesis is loaded. In other words, they approach each other. This approach movement can then likewise be damped via the further elastomer element. Depending on the size of the elastomer element, it is possible to determine the time at which the upper part and the lower part are coupled via the elastomer element. If the chosen elastomer element is so large that the upper part and the lower part already bear on the elastomer element when the prosthesis is unloaded, damping is in this way already provided after a slight inward spring movement. If one or both parts are spaced apart from the elastomer element when the foot prosthesis is unloaded, the damping effect necessarily begins only at a later time, when both have performed a sufficient inward spring movement.

In a refinement of the invention, the upper part, in the area near the heel, in particular in the area of the first and second upper-part portions, can have an elastomer inlay within the carbon fiber composite, which locally varies the bending properties of the latter. The carbon fiber composite is a multi-layer laminate. This easily allows an intermediate elastomer layer to be integrated into this laminate. According to this embodiment of the invention, this is done in the area of the upper part near the heel, and it is preferably situated in the area of the first and/or second upper-part portion, i.e. in the area of the deflection there. This elastomer inlay can preferably extend from the first into the second upper-part portion, i.e. can run through the deflection. Depending on how thick the chosen inlay is and on what Shore A hardness it has, it is possible to adjust the spring characteristic or flexural strength of this upper-part area to make it softer or harder.

In a refinement of the invention, provision can be made that the component, in the area near the heel, extends in particular with the second upper-part portion curved in the direction of the forefoot and converges with the upper-part portion, which comes from the forefoot and in the area near the heel is likewise curved in the direction of the forefoot, in order to form a securing portion for a connection means, in particular a pyramid adapter. The securing portion extends obliquely upward, relative to the extent of the lower part, and is oriented in the direction of the forefoot. To shape it in this way, it is necessary that the upper-part portion which runs from the forefoot to the securing portion and the upper-part portion which is near the heel (i.e., in the case of an S-shaped configuration, the second upper-part portion in the area near the heel) are likewise suitably curved, such that both converge and form the securing portion. The latter is sufficiently strong to form a safe fixing possibility for a connection means, for example a pyramid adapter, which is designed for attaching the prosthesis shaft. As an alternative to this, however, it is also conceivable to design the component with its securing portion extending vertically upward, such that this portion, coming from the upper end, branches into an upper-part portion extending to the forefoot, and an upper-part portion extending to the heel, e.g. to a spring geometry there.

In the area of the connection of the two upper-part portions, an elastomer element can be fitted that connects both portions.

Finally, in an expedient embodiment of the invention, provision is made that, in toe area between the upper part and the lower part, i.e. in the "component interior", a securing element is provided for a releasably insertable elastomer element which, during walking, couples the upper part to the lower part. This elastomer element, which preferably has an elongate design, is therefore a filling piece that is inserted between the upper part and lower part, i.e. can be integrated as and when required, but can also be permanently integrated there. During the walking movement, this elastomer element comes into contact with one with both mutually facing surfaces of the upper part and lower part, depending on the design of the elastomer element in terms of length and thickness. This therefore leads to a change in the contacting procedure or coupling procedure of the upper part with the lower part, which according to the invention are coupled via this elastomer element when the foot prosthesis is loaded, i.e. when the upper part travels sufficiently far inward in the direction of the lower part. The movement, during walking, of the upper part relative to the lower part is subjected to a resistance via the elastomer element on which both temporarily bear, and this results in a stiffening of the spring formed by upper part and lower part in the area between heel and forefoot. In other words, a stiffness-increasing connection is established not just during the walking movement when the upper part directly contacts the lower part, but much earlier than this namely when a surface contact is effected via the inserted elastomer filling piece.

This coupling time the coupling time can be adjusted by means of a suitable length or thickness of this preferably planar, tongue-like elastomer element which can optionally also be structured (e.g. with pyramid-like tapering elevations on one side or with a wave profile), in the same way that the flexural strength can of course also be adjusted by a suitable choice of material. That is to say, the hardness of the prosthesis is variable to this extent, which is in particular of advantage to the user, if this elastomer element can be inserted releasably. Indeed, the user can then decide how he wishes to adjust the hardness of the prosthesis. In this way, therefore, it is possible to make an individual adjustment as regards from which phase of the step cycle the hardness of the forefoot begins to increase overproportionally.

To make the releasable insertion as simple as possible, the securing element can have a latching projection which is preferably directed toward the lower part and which engages in a latching recess provided on the insertable elastomer element. That is to say, the user can latch or clip this elastomer element relatively easily into place. However, it is also conceivable, by means of a suitable mating configuration, for this elastomer element to be pushed from the side into a corresponding recess, etc.

The securing element is located in the area near the heel, preferably on the lower part. It is therefore located, if provided, in the area of the further deflection on the upper part the which the first upper-part portion is deflected into the second upper-part portion. If an elastomer element is now provided in the area of this deflection and engages around the latter, the securing portion can be shaped in such a way that the deflection-side elastomer element engages with a form fit in the securing portion, i.e. is likewise in abutment there, whereby finally the coupling to the lower part can be established.

If they are not releasable, the elastomer elements can be arranged on the component by suitable adhesive bonding. Since they are only fixed on one component, this means that these is no shortening of the spring path or spring lever at the time of manufacture, but only when, as intended, the respective other part engages on the elastomer element.

To form the elastomer elements, a suitable plastic material is used, as required, which has the desired Shore A hardness.

Further advantages, features and details of the invention will become clear from the illustrative embodiment described below and by reference to the drawings, in which.

Figure 1:
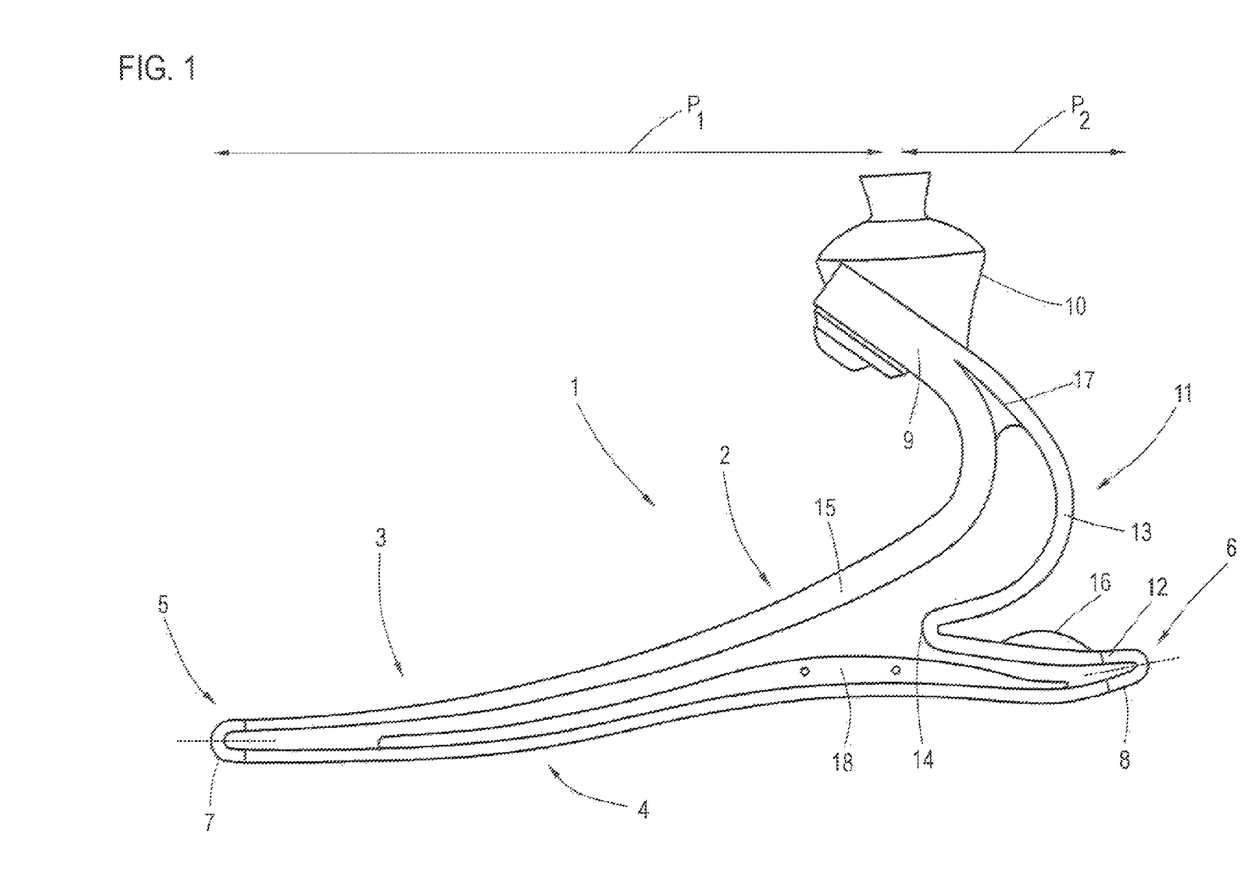
FIG. 1 shows a side view of a foot prosthesis according to the invention in a first embodiment.

FIG. 1 shows a foot prosthesis 1 according to the invention, comprising a one-piece carbon fiber composite component 2, which forms a spring and constitutes the central prosthesis component. On and by means of the component 2, two parts are formed that are to be distinguished in principle from each other, namely an upper part 3 and lower part 4, the two broken lines indicating the point to which the upper part 3 runs and the point to which the lower part 4 runs. Upper part 3 and lower part 4 are connected integrally to each other at the forefoot 5 and in the area of the heel 6, in each case via a respective deflection 7, 8, since the component 2, as has been stated, is in one piece and closed, and it therefore has no interruptions. The deflections 7, 8 are almost 180° in the area of the forefoot and slightly less in the area of the heel. In principle, a deflection should be in the range of between 135° and 180°.

On the upper part 3, a securing portion 9 is also formed on which a connection means 10, here a pyramid adapter, is provided for connection to a prosthesis shaft. As seen from the heel 6, this securing portion 9 extends approximately in the direction of the forefoot 5, i.e. is slightly inclined. The upper part 3 is obviously correspondingly shaped for this purpose, as will be discussed in detail below.

Moreover, in its upper-part area 11 near the heel, the upper part 3 has a spring portion, which is embodied by a first upper-part portion 12 and a second upper-part portion 13. The first upper-part portion 12 directly adjoins the deflection 8 and extends approximately in the direction of the forefoot. It runs into a further deflection 14, which should likewise be in the stated angle range, and then merges into the second upper-part portion 13, which in turn extends in a curve into the securing portion 9. The third upper-part portion 15, coming from the forefoot 5, also opens into the securing portion 9.

Therefore, a spring portion is clearly formed in the upper-part area 11 near the heel and permits an inward spring movement about the deflection 14. An almost S-shaped configuration is formed an inverted view of toe prosthesis from FIG. 1, as is shown by comparison in FIGS. 2-5).

The whole component 2 is made from a carbon fiber composite, in other words a multi-layer carbon fiber component, wherein the layered structure allows different thicknesses to be obtained, as is indicated in FIG. 1.

The central core of the foot prosthesis 1 is the one-piece, closed component 2. Upper part 3 and lower part 4 are connected to each other at the two outermost points, that is to say the forefoot 5 and the heel 6, by the deflections 7, 8, which are torsionally flexible with respect to the mediolateral axis, whereby upper part 3 and lower part 4 are also spaced apart from each other. In this way, the sole area, i.e. the lower part 4, is able to deform and twist homogeneously along the entire length of the foot. This ensures a homogeneous rollover since, in the course of the step cycle, i.e. from setting down the heel 6 to pushing off with the forefoot 5, the flexural strength of the area of the component 2 momentarily in contact with the ground does not abruptly change, because the one-part component 2, i.e. the one-part spring, offers an uninterrupted spring action. That is to say, the energy flow, resulting from the introduction of force by set-down on the ground and loading of the foot prosthesis 1, is not interrupted by any connection points rigidly connecting the upper part 3 to the lower part 4. Instead, the entire length of the prosthesis can be utilized for the spring movement, a maximum spring length or maximum spring excursions are provided. This is because upper part 3 and lower part 4 are connected to each other only via the deflections 7, 8.

This basic torsional flexibility leads to balanced pronation and supination and thereby permits good adaptation to different ground surfaces and also to unevenness of the ground.

When force is introduced vertically, the foot prosthesis has to deflect uniformly inward. The binding point of the foot prosthesis to the shaft and therefore to the leg of the amputee is obtained via the securing means 10. The latter also ultimately defines the two levers or lever lengths provided between this securing point and the forefoot 5 and the heel 6. These two lever lengths are shown by the two arrows P1 and P2. The lever running to the forefoot and indicated by the arrow P1 is clearly several times longer than the lever running to the heel 6 and indicated by the arrow P2. That is to say, the lever ratios between the pyramid adapter and the front and rear deflections 7, 8 are different. This lever imbalance is compensated in particular by the design of the upper-part area 11 with the deflection 14 and with the two upper-part portions 12, 13, which embody the spring portion there.

As will also be seen from FIG. 1, an elastomer element 16 is arranged on the outside of the first upper-part portion 12. When the spring portion formed by the S shape travels sufficiently inward, the second upper-part portion 13 comes into contact with the elastomer element 16, and its further movement 15 damped. The hardness of the heel area can be varied by this means.

Moreover, an elastomer element 17 is arranged between the second upper-part portion 13 and the curved part of the third upper-part portion 15, at the transition to the securing portion 9. This elastomer element 17 also serves to adjust the spring hardness in this area.

Finally, a third elastomer element 18 is provided on the lower part 4, which third elastomer element 18 is elongate and extends well over half the length of the lower part. It lies between the lower part 4 and the upper part 3 spaced apart from the latter. In the event of an inward spring movement, the first upper-part portion 12 and also the second upper-part portion 15 approach this elastomer element 18 and, as the inward spring movement continues, they come into contact with it, i.e. the continued inward spring movement is in turn damped. Thus, each time a component portion comes to bear in particular on the elastomer elements 16 and 18, there is a load-dependent increase in resistance and, as a result, a hardening of the prosthesis, it being possible for the time of this hardening to be adjusted according to the thickness of the respective elastomer element 16, 18.

FIGS. 2-5 show a further embodiment of a foot prosthesis 1 according to the invention, the same reference signs being used for identical components.

Figure 2:
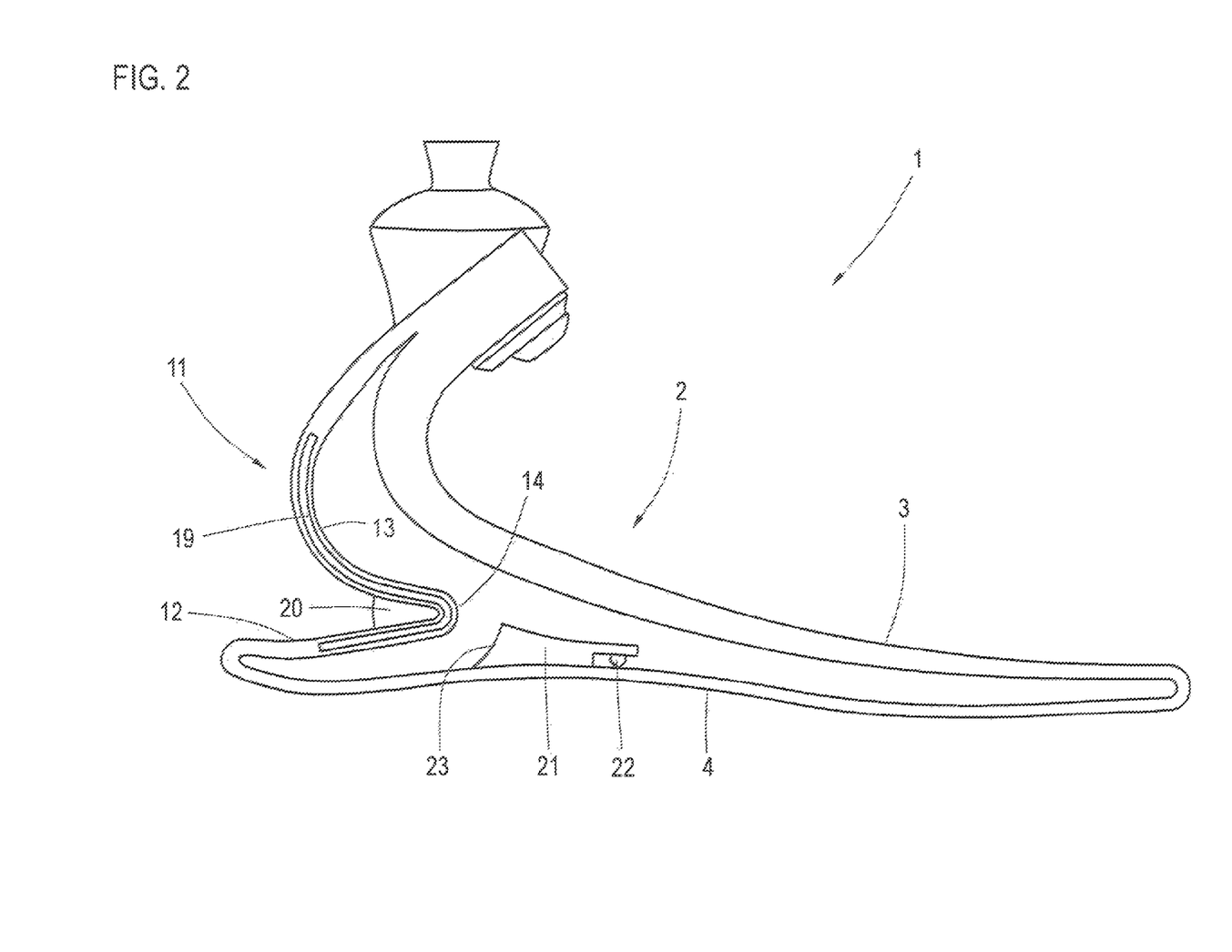
FIG. 2 shows side of a foot prosthesis according to the invention in a second embodiment, without integrated releasable elastomer elements.

FIG. 2 shows (in an inverted view compared to FIG. 1) the foot prosthesis 1 which, in terms of its basic shape, corresponds to the foot prosthesis 1 from FIG. 1.

Here, an elastomer inlay 19 is integrated into the carbon fiber composite laminate in the upper-part area 11 which, at the heel side, forms the additional spring portion. This elastomer inlay 19 extends from the first upper-part portion 12 via the deflection 14 into the second upper-part portion 13. In this way, the flexural strength and spring characteristic can thus be adjusted in this area. The elastomer inlay 19 is already integrated during the production of the component 2.

It will be seen that, in the area of the deflection 14, a further elastomer element 20 is integrated, which damps the movement of the first upper-part portion 12 relative to the second upper-part portion 13.

As FIG. 2 shows, a securing element 21 is arranged on the lower part 3, once again on the inner face here, and, as will be shown in detail below, different elastomer inlays can be fixed thereon. The securing element 21 has a latching projection 22, which is here oriented in the direction of the lower part 4. As will be discussed in detail below, a releasable elastomer element can be fixed on this latching projection 22.

On the other side, a semicircular abutment surface 23 is formed which serves to support an elastomer element that can be fitted releasably in the area of the deflection 14.

Figure 3:
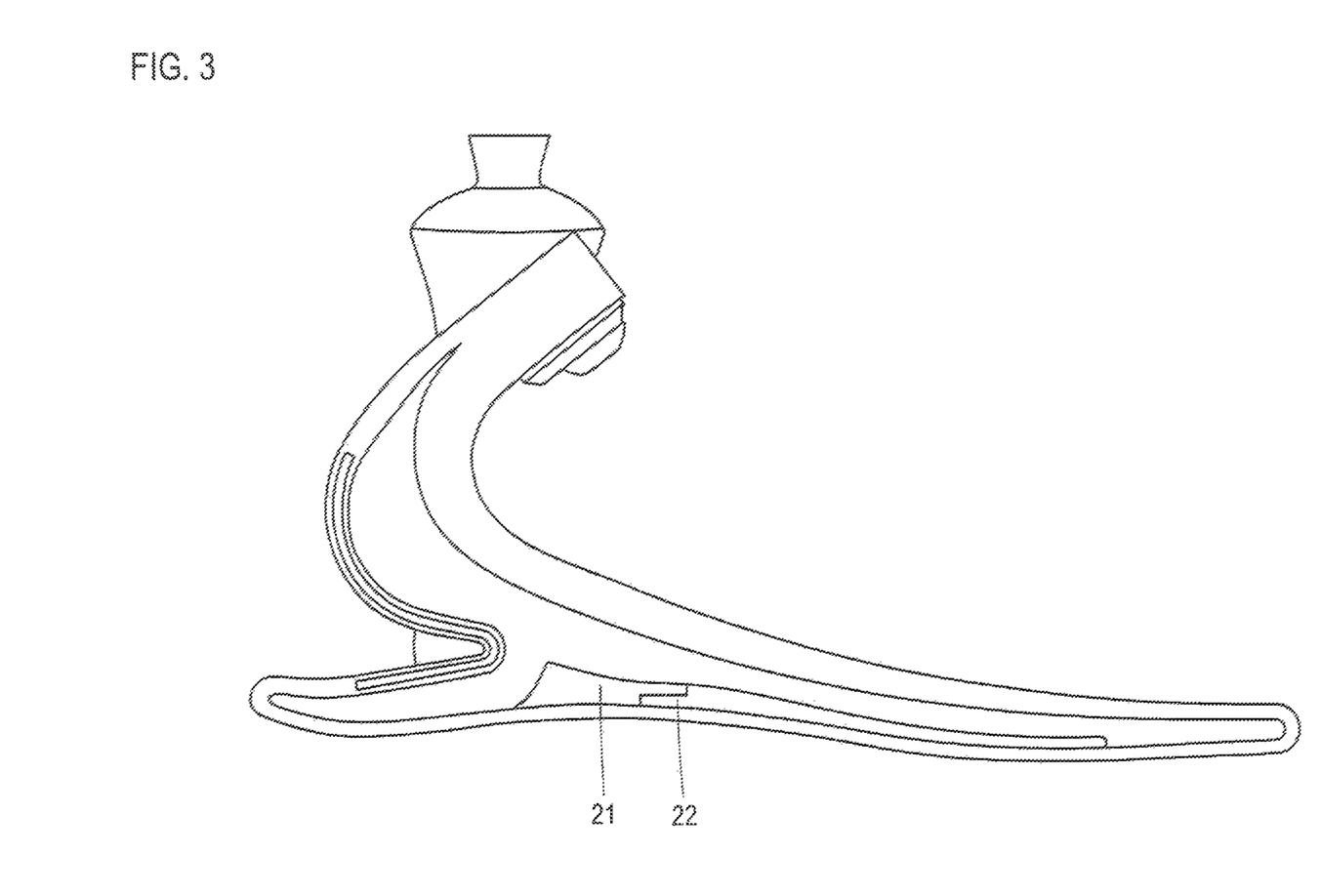
FIGS. 3-7 show the foot prosthesis from FIG. 2 with different integrated elastomer elements.

FIG. 3 shows the foot prosthesis 1 from FIG. 2, with a releasable elastomer element 24 arranged on the securing element 21. This elastomer element 24 has a latching recess (not shown) in which the latching projection 22 of the slightly elastic securing element engages. For fixing purposes, the portion of the securing element 21 supporting the latching projection can be bent slightly, for example, such that the elastomer inlay 24 can be pushed in and the latching projection 22, once released, can engage in the latching recess. This elastomer element 24 can be of any desired length and, in contrast to what is shown in FIG. 3, it can also be profiled, for example with triangular projections jutting toward the upper part or with basically an undulating shape, etc. It in any case affords the user the possibility of being able to vary the hardness in this area, by means of the elastomer element 24 being either inserted or removed, and it is of course also possible to use elastomer elements of different hardness or different length.

Figure 4:
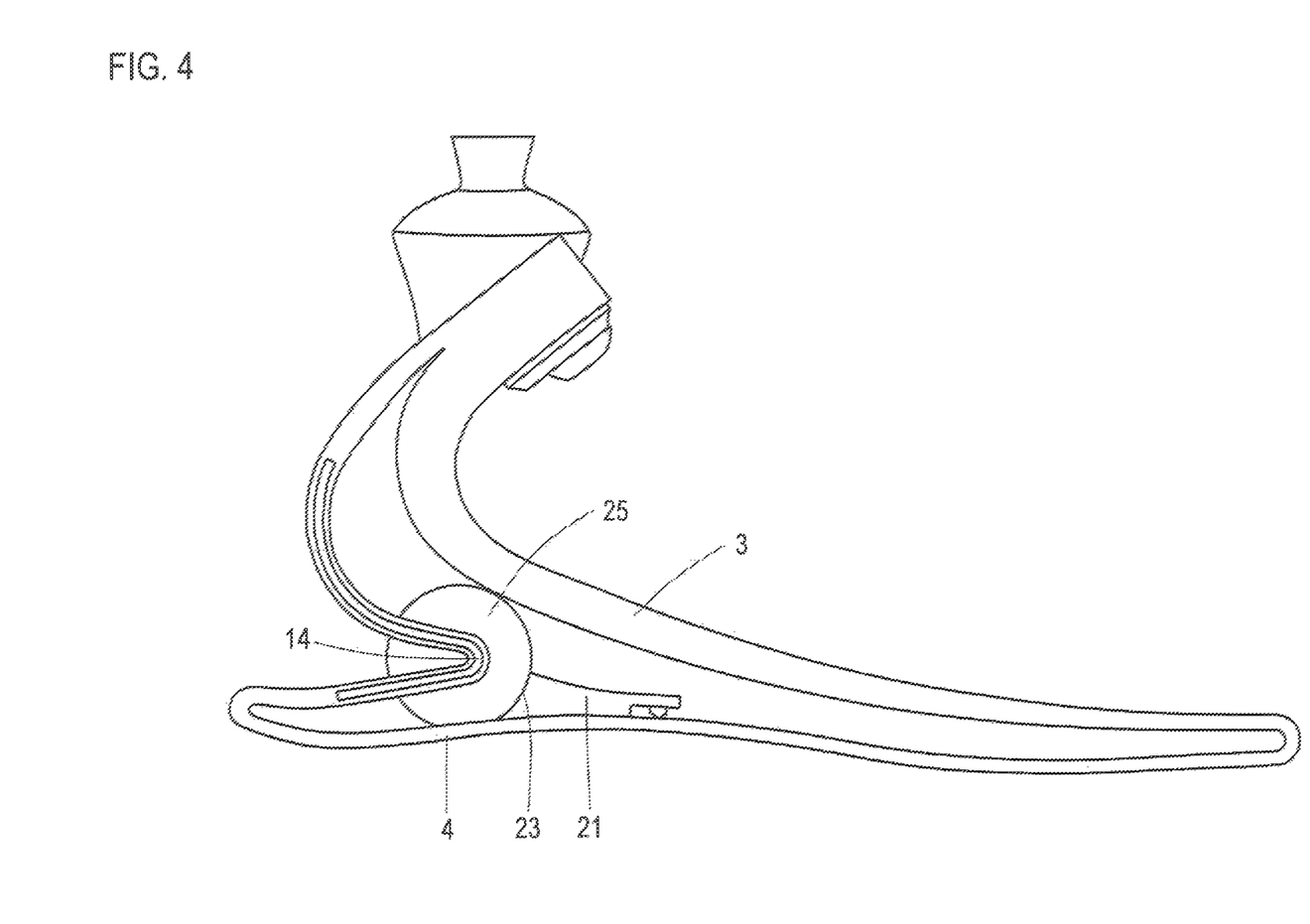

FIG. 4 shows the foot prosthesis 1 from FIG. 1, with a further elastomer element 25 being inserted which, in the example shown, has a round shape and engages around the deflection 14. It is supported on the abutment portion 23 of the securing element 21. It lies at the bottom on the lower part 4 and at the top on the upper part 3 but is connected to these only through contact and is not fixed to them. It clearly damps the inward spring movement upon loading of the foot prosthesis 1, when the upper part 3 moves in the direction of the lower part 4. Here too, the prosthesis hardness can be varied through elastomer elements 25 of different hardness. If the chosen elastomer element 25 is slightly narrower, such that it does not touch the upper part 3, the contact and therefore the hardening are obtained only when a sufficient inward spring movement has taken place.

Figure 5:
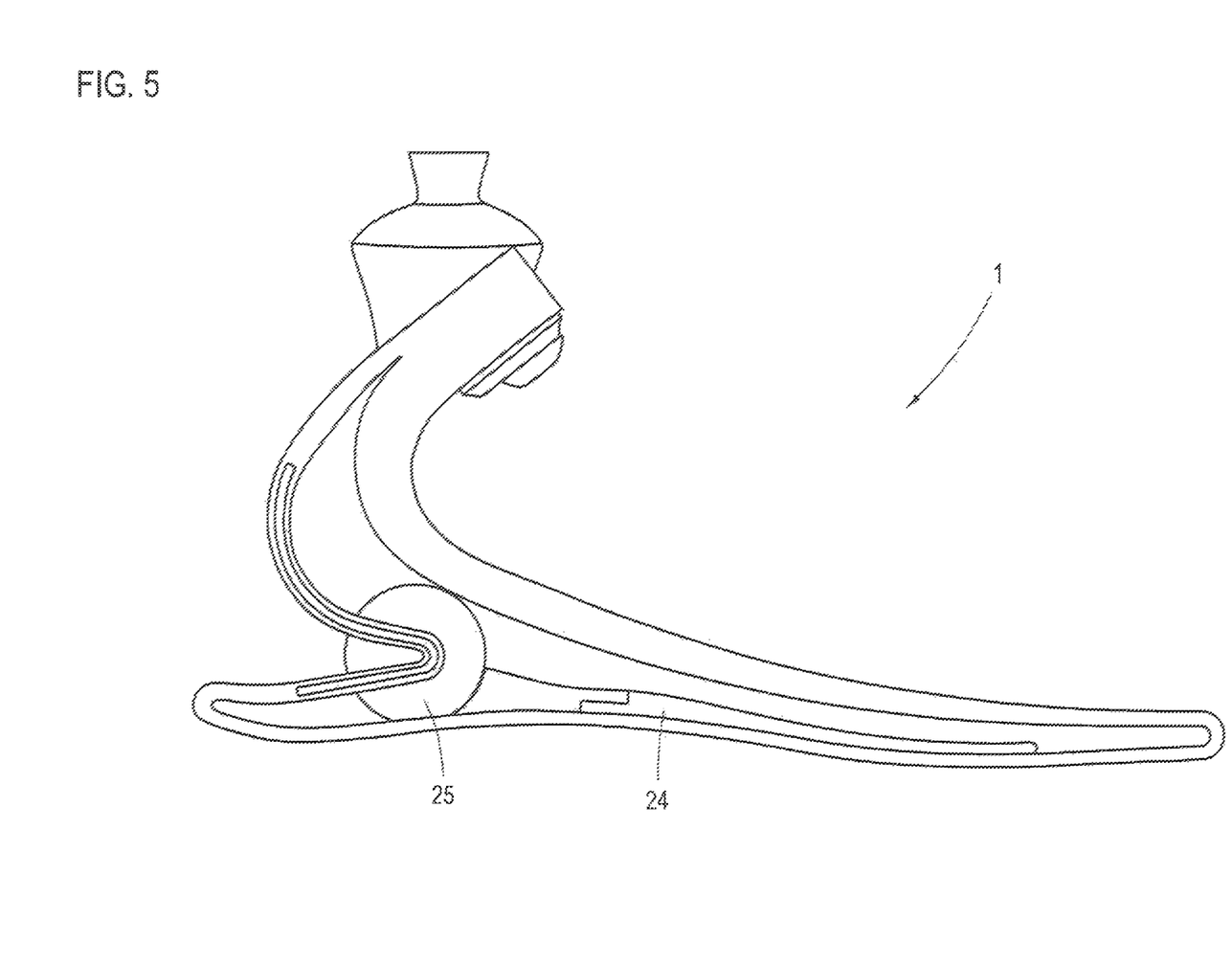

FIG. 5 finally shows the foot prosthesis 1 with both the elastomer element 24 and also the elastomer element 25 being inserted here.

Figure 6:
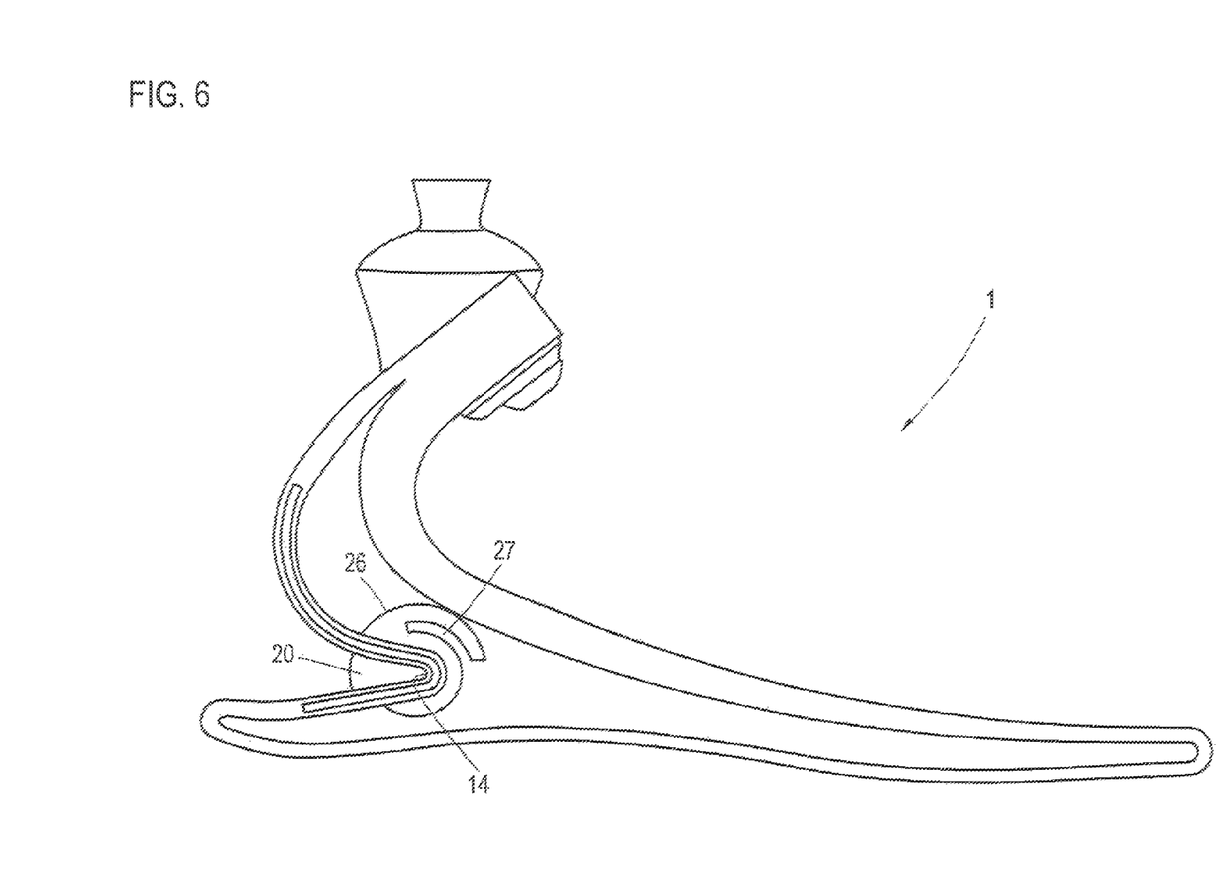
Figure 7:
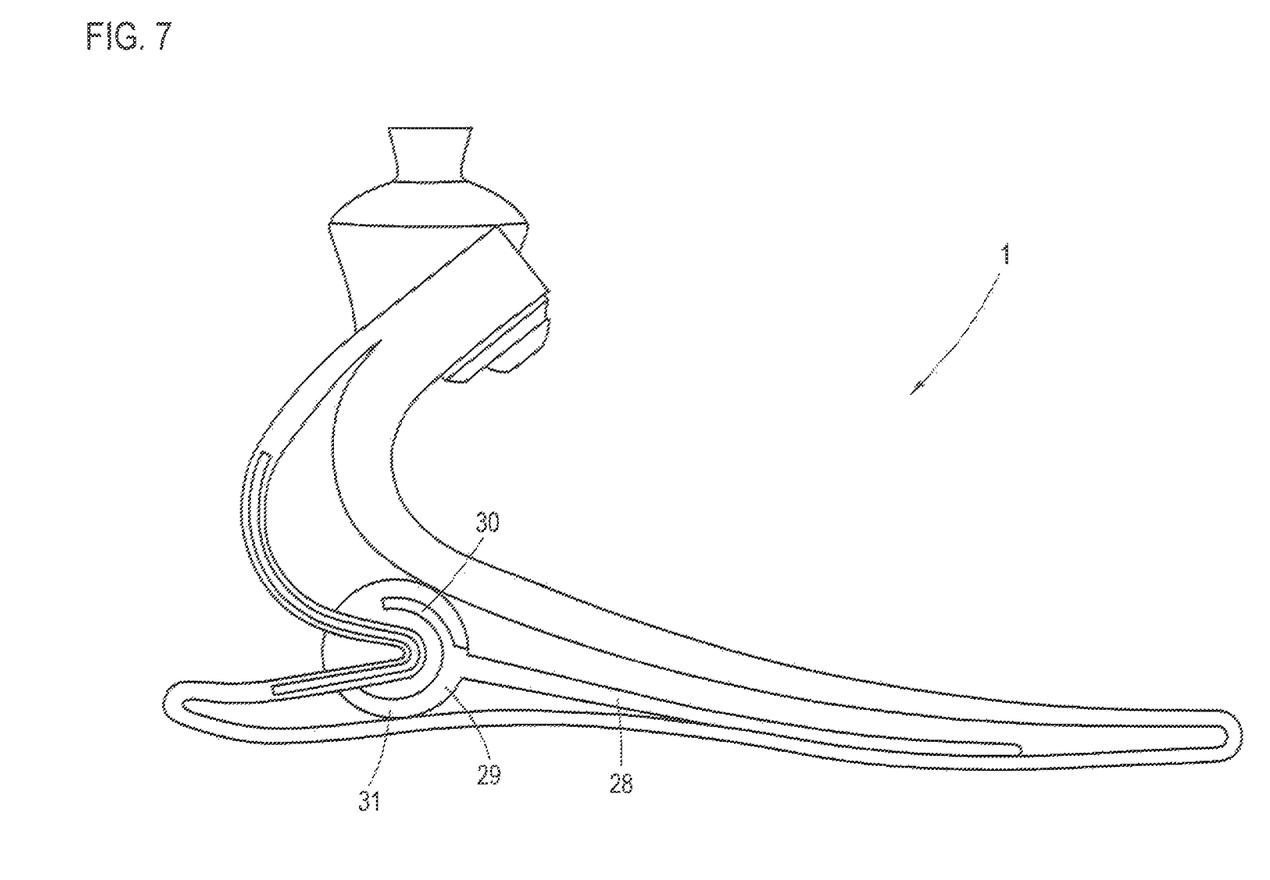

Finally, FIGS. 6 and 7 show a further embodiment of a foot prosthesis according to the invention, which differs from the above-described embodiments once again in terms of the elastomer elements that are used. FIG. 6 shows a foot prosthesis 1 which, in terms of its basic shape, corresponds to the above-described embodiments. At the rear, in the heel area, an elastomer element 20 is once again adhesively bonded, and, lying opposite it, and once again surrounding the deflection 14, an elastomer element 26 is arranged which is similar to the elastomer element 25 but has a slightly different geometry. It has a curved slit 27 which serves to fix an elongate elastomer element 28 which can be inserted from the side and which can be held on the elastomer element 26, as is shown in FIG. 7. The elastomer element 28 has a round securing portion 29 which, with one portion 30, engages in the round gap 27 and, with its other portion 31, engages around the underside of the elastomer element 26 and is supported on the lower part. Therefore, a special holding geometry is provided here which permits lateral insertion of the elastomer element 28.

The invention claimed is:

1. Foot prosthesis, comprising an upper part, and a lower part that is placed on the ground when walking, the upper part extends above the lower part at a distance therefrom, the upper part and the lower part form a spring and move relative to each other during walking, wherein the spring formed by the upper part and the lower part is a carbon fiber composite component formed as only one piece and closed, the carbon fiber composite component is made from a carbon fiber composite and includes a forefront and a heel, the upper part, in an area near the heel, includes an elastomer inlay within the carbon fiber composite component, the carbon fiber composite component is a laminate having a plurality of layers of the carbon fiber composite, and the elastomer inlay is an intermediate elastomer layer integrated within the laminate.

2. Foot prosthesis according to claim 1, wherein the carbon fiber composite component, in an area of the upper part near the heel, has a deflection, in such a way that a first upper-part portion extending above the lower part merges via the deflection into a second upper-part portion extending above the first upper-part portion, and the elastomer inlay extends from the first upper-part portion through the deflection and into the second upper-part portion.

3. Foot prosthesis according to claim 2, wherein, in the area of the deflection, an elastomer element is fitted on one or both of the first upper-part portion and the second upper-part portion.

4. Foot prosthesis according to claim 2, wherein, in an area between the upper part and the lower part, an elastomer element that engages around the deflection and contacts the upper part to the lower part, at least during walking, is provided.

5. Foot prosthesis according to claim 4, wherein the elastomer element is releasably inserted around the deflection.

6. Foot prosthesis according to claim 2, wherein the elastomer inlay is disposed in an area of at least one of the first upper-part portion and the second upper-part portion.

7. Foot prosthesis according to claim 1, wherein the carbon fiber composite component, in an area near the heel, extends with an upper-part portion curved in the direction of the forefoot and converges with another upper-part portion, which comes from the forefoot and in the area near the heel is likewise curved in the direction of the forefoot, in order to form a securing portion for a connection means.

8. Foot prosthesis according to claim 7, wherein, in an area where the upper-part portion converges with the another upper-part portion, an elastomer element is fitted that connects to both portions.

9. Foot prosthesis according to claim 7, wherein the connection means is a pyramid adapter.

10. Foot prosthesis according to claim 1, wherein, in an area between the upper part and the lower part, a securing element is provided for an elastomer element, wherein the elastomer element, at least during walking, contacts the upper part and the lower part.

11. Foot prosthesis according to claim 10, wherein the securing element has a latching projection which engages in a latching recess provided on the insertable elastomer element.

12. Foot prosthesis according to claim 11, wherein the latching projection is directed toward the lower part.

13. Foot prosthesis according to claim 10, wherein the elastomer element is releasably insertable on the securing element.

14. Foot prosthesis according to claim 1, wherein the upper part and the lower part merge into each other at the forefoot and the heel, in each case via a deflection of the component in the range of between 135° and 180°.

15. Foot prosthesis, comprising an upper part, and a lower part that is placed on the ground when walking, the upper part extends above the lower part at a distance therefrom, the upper part and the lower part form a spring and move relative to each other during walking, wherein the spring formed by the upper part and the lower part is a carbon fiber composite component formed as only one piece and closed, the carbon fiber composite component is made from a carbon fiber composite and includes a forefront and a heel, the upper part, in an area near the heel, includes an elastomer inlay within the carbon fiber composite component, wherein the carbon fiber composite component, in an area near the heel, extends with an upper-part portion curved in the direction of the forefoot and converges with another upper-part portion, which comes from the forefoot and in the area near the heel is likewise curved in the direction of the forefoot, in order to form a securing portion for a connection means, and in an area where the upper-part portion converges with the another upper-part portion, an elastomer element is fitted that connects to both portions.

16. Foot prosthesis, comprising an upper part, and a lower part that is placed on the ground when walking, the upper part extends above the lower part at a distance therefrom, the upper part and the lower part form a spring and move relative to each other during walking, wherein the spring formed by the upper part and the lower part is a carbon fiber composite component formed as only one piece and closed, the carbon fiber composite component is made from a carbon fiber composite and includes a forefront and a heel, the upper part, in an area near the heel, includes an elastomer inlay within the carbon fiber composite component, wherein, in an area between the upper part and the lower part, a securing element is provided for an elastomer element, wherein the elastomer element, at least during walking, contacts the upper part and the lower part, and the elastomer element is releasably insertable on the securing element.

* * * * *